US009810614B2

(12) United States Patent
Saussine et al.

(10) Patent No.: US 9,810,614 B2
(45) Date of Patent: Nov. 7, 2017

(54) METHOD FOR EVALUATING THE COMPACTNESS OF A LAYER OF RAILWAY LINE BALLAST, DEVICE FOR IMPLEMENTING SAME AND METHOD FOR PREDICTING THE COMPACTION OF SAID LAYER OF BALLAST

(71) Applicants: SNCF RESEAU, Paris (FR); UNIVERSITE DE MONTPELLIER 2 SCIENCES ET TECHNIQUES, Montpellier (FR); UNIVERSITE BLAISE PASCAL-CLERMONT II, Clermont Ferrand (FR); LE CENTRE NATIONAL DE LA RECHERCHE SCIENTIFIQUE (CNRS), Paris (FR)

(72) Inventors: Gilles Saussine, Issy les Moulineaux (FR); Juan Carlos Quezada, Malakoff (FR); Pierre Breul, Corent (FR); Franck Radjai, Montpellier (FR)

(73) Assignees: SNCF RESEAU, Paris (FR); UNIVERSITE DE MONTPELLIER 2 SCIENCES ET TECHNIQUES, Montpellier (FR); UNIVERSITE BLAISE PASCAL-CLERMONT II, Clermont Ferrand (FR); LE CENTRE NATIONAL DE LA RECHERCHE SCIENTIFIQUE (CNRS), Paris (FR)

(*) Notice: Subject to any disclaimer, the term of this patent is extended or adjusted under 35 U.S.C. 154(b) by 138 days.

(21) Appl. No.: 14/439,544

(22) PCT Filed: Oct. 28, 2013

(86) PCT No.: PCT/FR2013/000280
§ 371 (c)(1),
(2) Date: Apr. 29, 2015

(87) PCT Pub. No.: WO2014/068199
PCT Pub. Date: May 8, 2014

(65) Prior Publication Data
US 2015/0293000 A1    Oct. 15, 2015

(30) Foreign Application Priority Data
Oct. 30, 2012 (FR) ...................................... 12 02928

(51) Int. Cl.
*G01N 3/48* (2006.01)
*E01B 35/00* (2006.01)
(Continued)

(52) U.S. Cl.
CPC ............... *G01N 3/48* (2013.01); *E01B 35/00* (2013.01); *E02D 1/022* (2013.01); *G01N 3/40* (2013.01);
(Continued)

(58) Field of Classification Search
CPC ......... E01B 27/12; E01B 35/00; E02D 1/022; G01N 2203/001; G01N 33/42; G01N 3/40; G01N 3/48; G01N 2203/0082
See application file for complete search history.

(56) References Cited

U.S. PATENT DOCUMENTS 2,713,975 A  *  7/1955  Martin ...................... E01B 5/16
                                                    238/297
3,807,311 A     4/1974  Plasser et al.
(Continued)

FOREIGN PATENT DOCUMENTS

CN        2585882 Y     11/2003
FR     2 145 920 A5      2/1973
(Continued)

OTHER PUBLICATIONS
International Search Report dated Jan. 28, 2014 issued in corresponding application No. PCT/FR2013/000280.

*Primary Examiner* — Francis Gray
(74) *Attorney, Agent, or Firm* — Westerman, Hattori, Daniels & Adrian, LLP (57) ABSTRACT

The method for evaluating the compactness of a layer of railroad ballast near a railroad tie includes at least one step of taking at least two measurements (11,11a,11b) of the penetration resistance (Qd) of the ballast (13) near one and the same railroad tie (10), and a step of calculating the mean value ($Qd_{mean}$) of these measurements (11,11a,11b) of penetration resistance (Qd). Also provided are a device for implementing such a method and a method for predicting the settlement of the ballast of a railroad track including a step of evaluating the compactness of a ballast near a railroad tie.

23 Claims, 2 Drawing Sheets

(51) Int. Cl.
  *G01N 3/40*   (2006.01)
  *E02D 1/02*   (2006.01)
  *G01N 33/42*  (2006.01)
  *E01B 27/12*  (2006.01)

(52) U.S. Cl.
  CPC .............. *G01N 33/42* (2013.01); *E01B 27/12* (2013.01); *G01N 2203/001* (2013.01); *G01N 2203/0082* (2013.01)

(56) References Cited

U.S. PATENT DOCUMENTS

| | | | | |
|---|---|---|---|---|
| 3,878,987 | A | * | 4/1975 | Uzuka ..................... E01B 1/008 104/11 |
| 4,040,292 | A | * | 8/1977 | Theurer .................. E01B 27/16 104/12 |
| 4,063,516 | A | * | 12/1977 | Theurer ................ E01B 27/027 104/12 |
| 5,726,349 | A | * | 3/1998 | Palmertree .............. E02D 1/022 73/84 |
| 6,062,090 | A | * | 5/2000 | Bachhuber .............. E02D 1/022 73/784 |

FOREIGN PATENT DOCUMENTS

| | | | |
|---|---|---|---|
| FR | 2 299 202 | A1 | 8/1976 |
| FR | 2 817 344 | A1 | 5/2002 |

* cited by examiner

METHOD FOR EVALUATING THE COMPACTNESS OF A LAYER OF RAILWAY LINE BALLAST, DEVICE FOR IMPLEMENTING SAME AND METHOD FOR PREDICTING THE COMPACTION OF SAID LAYER OF BALLAST

The invention relates mainly to a method for evaluating the compactness of a layer of railroad ballast.

The invention also relates to a device for implementing such a method.

The invention relates finally to a method for predicting the settlement of the ballast of a railroad track including a step of evaluating the compactness of the ballast.

The separation of the parallel rails of a railroad track is kept constant by railroad ties uniformly arranged perpendicular to the rails. The railroad ties are also able to spread the load transmitted by the rails.

A layer of ballast situated underneath and between each railroad tie supports the railroad track. The ballast is a granular material obtained from crushing rocks extracted from quarries from which hard stone, for example granite diorite, rhyolite, quartzite or sandstone is quarried.

The ballast performs a number of functions. Notably, it provides the longitudinal and lateral anchorage of the railroad track. It also damps mechanical and acoustic vibrations caused by the circulation of the trains. It also transmits the load applied to the railroad ties to the platform consisting of the natural layer of the ground, limiting the compacting of the track. Finally, it makes the operations of maintaining and laying the track easier and contributes to the drainage of rainwater.

The circulation of trains along the track causes the ballast to progressively settle because of the progressive rearrangement of the granular material of which the ballast is made. This settlement gives rise to track defects notably characterized by sinking of the railroad ties into the material.

It is known practice to correct these defects using various upkeep and maintenance operations. Of notable mention are the operations of tamping, packing or dynamic stabilization. These operations allow the defects to be corrected by vibrating and packing the grains constituting the ballast and situated under the railroad ties, allowing the track to be returned to its initial profile by correcting the longitudinal and transverse leveling.

However, these operations cannot be carried out until the defects become significant. As a result, there is a period of time during which trains run along deformed tracks.

To date, and so far as the Applicants are aware, there is no method in existence for predicting the settlement of the ballast of a railroad track.

Moreover, creating a method for predicting the settlement of the ballast of necessity entails evaluating and characterizing the way in which the ballast behaves.

To this end, publication FR7602166 discloses how to measure the density of the ballast of a railroad track. To do that, the time taken for a penetration tool to penetrate the ballast until it reaches a defined depth is measured. Tamping or leveling operations are either performed or not performed according to the density measured.

While this method does allow the state of the ballast to be measured at a given instant, it does not allow the way in which the settlement of the ballast will evolve over time to be predicted.

Moreover, the system used to apply this method is of necessity mounted on a mobile damping machine, needs to be multiplied in order to have several measurement points and needs therefore to be associated with an acquisition system.

That being the case, the present invention targets an alternative method for evaluating the compactness of a layer of railroad ballast and a device for implementing this method which can be mounted on any maintenance machine.

The invention also targets a method for predicting the settlement of a layer of railroad ballast.

To this end, the method for evaluating the compactness of a layer of railroad ballast near a railroad tie of the invention is essentially characterized in that it comprises at least one step of taking at least two measurements of the penetration resistance of the ballast near one and the same railroad tie, and a step of calculating the mean value of these measurements of penetration resistance.

The method of the invention may also comprise the following optional features considered in isolation or in any technically feasible combinations:

- each measurement of penetration resistance is taken at a maximum distance of five centimeters away from the railroad tie and on each side of said railroad tie.
- the measurements of penetration resistance are separated from one another by at least fifteen centimeters.
- each measurement of penetration resistance is taken at a maximum distance of five centimeters away from the rail.
- the method may comprise at least one step of taking four measurements of the penetration resistance of the ballast near one and the same railroad tie, each measurement being performed on the outside of the rail, on each side of the railroad tie and near the intersection between the railroad tie and the rail.
- the method may comprise at least one step of taking eight measurements of the penetration resistance of the ballast near one and the same railroad tie, four first measurements being performed on each side of the railroad tie on the outside of the rail near the intersection between the railroad tie and the rail, and four second measurements being performed on the inside of the rail near the intersection between the railroad tie and the rail.
- each measurement of the penetration resistance of the ballast near a railroad tie is carried out using a dynamic penetrometer comprising a striking head onto which a mass falls at least once to drive into the ballast a conical penetration tip situated at the opposite end from the striking head and connected to the latter by a rod, and a computer determines the instantaneous penetration resistance of the ballast using the following formula:

$$Qd_i = \frac{E}{A \times e}$$

where $Qd_i$ is the instantaneous penetration resistance for one strike,

E is the energy received on the striking head, expressed in J,

A is the cross section of the tip expressed in square meters, e is the depth to which the conical tip is driven, expressed in meters, and the computer averages all the instantaneous penetration resistance values obtained in order to determine the penetration resistance.

each measurement of the penetration resistance of the ballast near a railroad tie is carried out using a static penetrometer for which the driving of the penetrometer is carried out by means of a vertical driving ram, and a computer determines the compactness of the ballast using the following formula:

$$Qd_i = \frac{F}{A}$$

where $Qd_i$ is the instantaneous penetration resistance of the penetrometer per drive,
A is the cross section of the penetration tip expressed in square meters, and
F is the thrust force applied to the penetrometer, expressed in newtons,
and the computer averages all the instantaneous penetration resistance values obtained in order to determine the penetration resistance.

The invention also relates to a method for predicting the settlement of a layer of railroad ballast, which is essentially characterized in that it comprises at least one step of evaluating the compactness of a layer of railroad ballast by determining the mean value of the penetration resistance of the ballast near a railroad tie according to the method as defined hereinabove, and a step of predicting the settlement of said layer of ballast by applying the following formula:

$$\tau_N = \tau_\infty \left(1 - \frac{1}{1 + B\ln\left(1 + \frac{N}{No}\right)}\right)$$

where $\tau_N$ indicates the change in settlement of the layer of ballast as a function of N which is the number of axle passes over the railroad tie in question,
where No corresponds to the following formula:

$$No = a \times \ln\left(\frac{Qd_{0mean}}{p}\right) + b$$

where a is comprised between 46 and 57, and b is comprised between 40 and 50,
where $Qd_{0mean}$ is the penetration resistance determined in the step of evaluating the compactness of the layer of ballast, and taken at the end of maintenance operations or at the time of laying the railroad track, and
where p is the pressure under the railroad tie in question, expressed in megapascals,
in which $\tau_\infty$ corresponds to the following formula:

$$\tau_\infty = Ho(c \times \Gamma + e)$$

where c is comprised between 21 and 32, and e is comprised between 0.0040 and 0.006,
where Ho is the thickness of the layer of ballast considered, expressed in millimeters, and
where $\Gamma$ is the reduced intensity of the vibrations to which the ballast is subjected near the railroad tie in question and corresponds to the following formula:

$$\Gamma = \frac{Aw^2}{\frac{pd^2}{m} + g}$$

where A is the amplitude of the elastic vertical sinking of the track, calculated from a mechanical model or measured, expressed in meters,
where $w^2 = 2\pi f$, f being the frequency of passage of the bogies in hertz,
where p is the load applied by the railroad tie in question to the ballast, expressed in pascals,
where d is the mean diameter of a grain of ballast, expressed in meters, and
where m is the mass of a grain of the ballast, expressed in kilograms, and
where B corresponds to the following formula:

$$B = h \times \Gamma^i$$

where h is comprised between 0.0003 and 0.0014, and i is comprised between −0.3 and −1.15,
where $\Gamma$ is the reduced intensity of the vibrations to which the ballast is subjected near the railroad tie in question.

The invention also relates to a device for implementing the method for evaluating the compactness of a layer of railroad ballast near a railroad tie as defined hereinabove and which is essentially characterized in that it comprises at least two static penetrometers able to be driven into the ballast near one and the same railroad tie, the driving of each penetrometer being carried out by means of a vertical driving ram, and a computer determines the compactness of the ballast using the following formula:

$$Qd_i = \frac{F}{A}$$

where $Qd_i$ is the instantaneous penetration resistance of the penetrometer per drive,
A is the cross section of the penetration tip in square meters, and
F is the thrust force applied to the penetrometer, expressed in newtons,
and the computer averages all the instantaneous penetration resistance values obtained in order to determine the penetration resistance.

The method of the invention may also comprise the following optional features considered in isolation or in any technically feasible combinations:
  the device comprises a frame intended to be positioned vertically facing and some distance away from the railroad track, and comprising at least four penetrometers fixed to said frame and of which the relative positions allow four measurements of the penetration resistance of the ballast near one and the same railroad tie to be carried out.
  the rate at which each penetrometer is driven down by each vertical driving ram is less than 3 centimeters per second.
  at least two penetrometers intended to measure the penetration resistance on the same side of a railroad tie are arranged with a lateral positioning ram which allows the lateral positioning of the two penetrometers in question.

Further features and advantages of the invention will become clearly apparent from the description thereof given hereinafter by way of nonlimiting indication, with reference to the attached figures in which.

The method for predicting the settlement of a layer of railroad ballast according to the invention comprises a first step consisting in evaluating the compactness of the layer of ballast.

In order to do that, according to the invention, at least two measurements of the penetration resistance of the ballast near a railroad tie are carried out, these measurements making it possible to evaluate the compactness of the ballast under the railroad ties.

Figure 1:
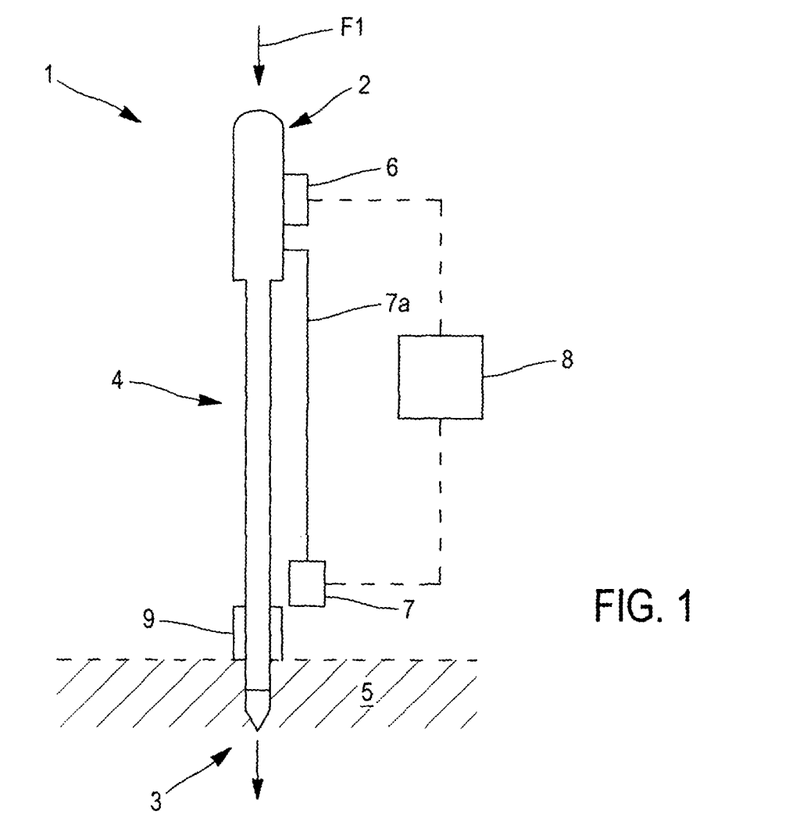
FIG. 1 is a schematic depiction of a penetrometer used in the method and the device of the invention for determining the penetration resistance of the ballast.

With reference to FIG. 1, the apparatus used for performing this measurement of the penetration resistance may be a dynamic penetrometer of the kind described in patent publication FR2817344 and marketed under the trademark PANDA®.

This penetrometer 1 comprises a striking head 2 connected to a conical penetration tip 3 by a string of rods 4. The conical penetration tip 3 is intended to be driven into the ground 5 under automatic action or by an operator striking the striking head toward the ground in the direction of the arrow F1. The load transmitted to the conical penetration tip 3 causes this conical penetration tip 3 to be driven into the ground in the direction of the arrow F2 to a greater or lesser extent according to the compactness of the ground.

The penetrometer 1 also comprises strain gauges 6 situated at the striking head 2, which indicate the energy transmitted by the impact as a function of the deformation of the strain gauges 6.

The penetrometer 1 also comprises a central acquisition unit 7 which is connected to the striking head by a belt 7a and which measures the extent to which the conical penetration tip 3 is driven into the ground 5. The central acquisition unit 7 and the strain gauges 6 are connected to a computer 8 which determines the penetration resistance of the ballast.

The way in which the penetrometer 1 works is as follows. An operator imparts a first blow to the striking head 2 in the direction of the arrow F1. The energy transmitted by the impact on the striking head 2 is measured on the basis of the deformation of the strain gauges 6, which deformation is transmitted to the acquisition unit 7.

At the same time, the conical penetration tip 3 is driven into the ground 5 in the direction of the arrow F2 by a depth of penetration that is measured by the acquisition unit 7. The measured depth after impact and the energy supplied are transmitted to the computer 8.

The computer then determines the instantaneous penetration resistance of the ballast using the following formula:

$$Qd_i = \frac{E}{A \times e}$$

where $Qd_i$ is the instantaneous penetration resistance for one strike,

E is the energy received on the striking head, expressed in J,

A is the cross section of the conical penetration tip, expressed in square meters, e is the depth to which the conical penetration tip is driven, expressed in meters.

Next, the operator strikes a second blow on the striking head. The computer then determines the instantaneous penetration resistance $Qd_i$ associated with this second blow.

At the end of the successive striking operations, the computer 8 averages all the instantaneous penetration resistance values $Qd_i$ obtained in order to determine the penetration resistance Qd.

The greater the number of blows struck on the penetrometer, the more accurate will be the value of the penetration resistance Qd. This is why it is preferable for the operator to exert control over the mean penetration per blow so that it is comprised between 5 and 10 millimeters.

This dynamic penetrometer 1 is particularly well suited to measuring the compactness of the ballast of a railroad track because of its small size stemming from the fact that its operation relies on the application of variable amounts of energy and that it is possible therefore to adapt the energy supplied to the striking head to suit the conditions of the measurement site.

As an alternative, it is equally possible to use a penetrometer of the static type for which the driving is performed by actuation of a vertical driving ram. In that case, the instantaneous penetration resistance $Qd_i$ is determined using the following formula:

$$Qd_i = \frac{F}{A}$$

where $Qd_i$ is the instantaneous penetration resistance of the penetrometer per drive, A is the cross section of the penetration tip expressed in square meters, and F is the thrust force applied to the penetrometer, expressed in newtons.

Like with the dynamic penetrometer, the penetration resistance value Qd of the ballast is determined by averaging the instantaneous penetration resistance values $Qd_i$ obtained during the successive penetrations of the penetrometer.

It should be noted that, with regard to the nature of the ballast, the rate at which the static penetrometer is driven in needs to be less than 3 centimeters per second. This is because upwards of a rate of 3 centimeters per second, the overestimating of penetration resistance is too great.

According to the method of the invention, this measuring of the penetration resistance Qd of the ballast, whether performed by striking using a penetrometer of the dynamic type, or by a penetration thrust force using a penetrometer of the static type, needs to be carried out at at least two points near a railroad tie. The penetration resistance values Qd associated with these two points are then averaged in order to evaluate the mean penetration resistance $Qd_{mean}$ under a railroad tie.

Figure 2:
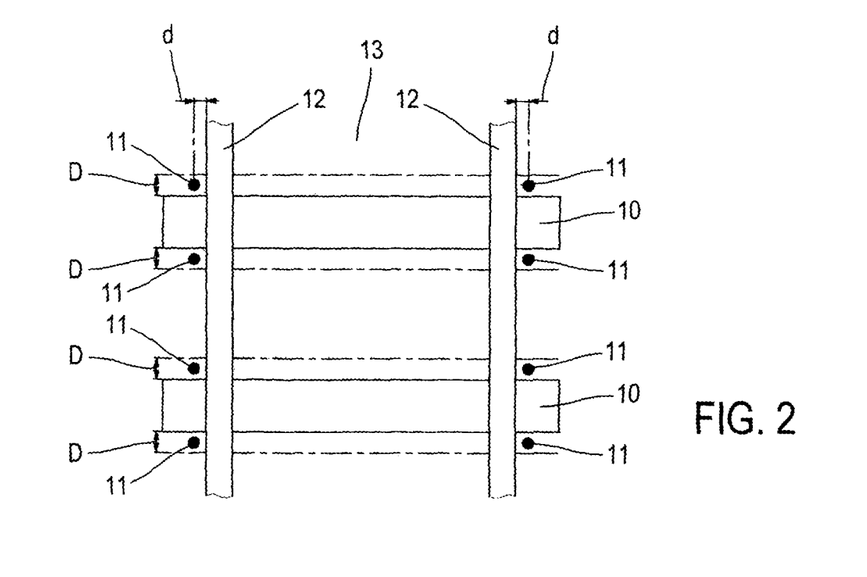
FIG. 2 is a schematic depiction from above of a railroad track on which are symbolized, per railroad tie, four measurement points for measuring the penetration resistance of the ballast according to a first alternative form of the method of the invention.

More specifically and with reference to FIG. 2, according to a first alternative form of the method of the invention, four penetration resistance measurements Qd are taken near a railroad tie 10. FIG. 2 depicts the points of impact 11 of the penetrometer 1 with the ground reflecting the penetration resistance measurements Qd.

Each measurement 11 has to be performed at a distance D at most equal to 5 centimeters away from the railroad tie 10.

Moreover, a minimum distance of 15 centimeters needs to be respected for two compactness measurements 11.

Furthermore, it is preferable for each measurement 11 to be situated a distance of at most 5 centimeters away from the rail 12.

With reference to FIG. 2, each measurement 11 is performed on the outside of the rail 12 near the intersection between the railroad tie 10 and the rail 12. As a result, according to this embodiment, four compactness measurements are carried out near one and the same railroad tie 10.

These four measurements are averaged in order to determine the mean penetration resistance $Qd_{mean}$ near the railroad tie in question and thus evaluate the settlement of this railroad tie 10.

Figure 3:
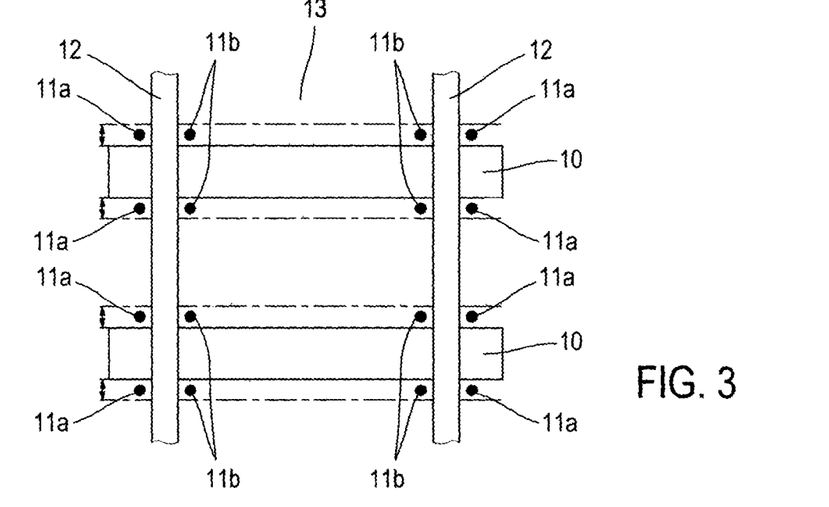
FIG. 3 is a schematic depiction from above of a railroad track on which are symbolized, per railroad tie, eight measurement points for measuring the penetration resistance of the ballast according to a second alternative form of the method of the invention.

According to a second alternative form of the method of the invention, and with reference to FIG. 3, eight measurements of the penetration resistance of the ballast are taken near one and the same railroad tie 10.

Four first measurements referenced 11a in FIG. 3 corresponding to four points of impact 11a of the penetrometer 1 are performed as in the first alternative form, on the outside of the rail 12 near the intersection between the railroad tie 10 and the rail 12. Four second measurements referenced 11b are performed on the inside of the rail 12 near the intersection between the railroad tie 10 and the rail 12. These eight measurements 11a, 11b also respect a maximum distance of 5 centimeters away from the railroad tie 10.

They are moreover spaced at least 15 centimeters apart and situated at a distance d of at most 5 centimeters away from the rail 12.

According to the invention, at least two measurements of the penetration resistance Qd need to be performed near one and the same railroad tie 10. If two penetration resistance measurements Qd are taken, these need to be taken one on each side of the railroad tie in order to be able as accurately as possible to estimate the state of compactness of the ballast under this railroad tie.

Moreover, whatever the number of penetration resistance measurements, these measurements may be taken either simultaneously or in succession.

Thus, according to the invention, several measurements of the penetration resistance Qd of the ballast near a railroad tie 10 make it possible to define the degree of compactness of the ballast 13 under the railroad ties 10. Siting these measurements in the way defined hereinabove is important because these measurements need to provide an estimate of the mechanical state of the ballast 13 under each railroad tie 10.

Figure 4:
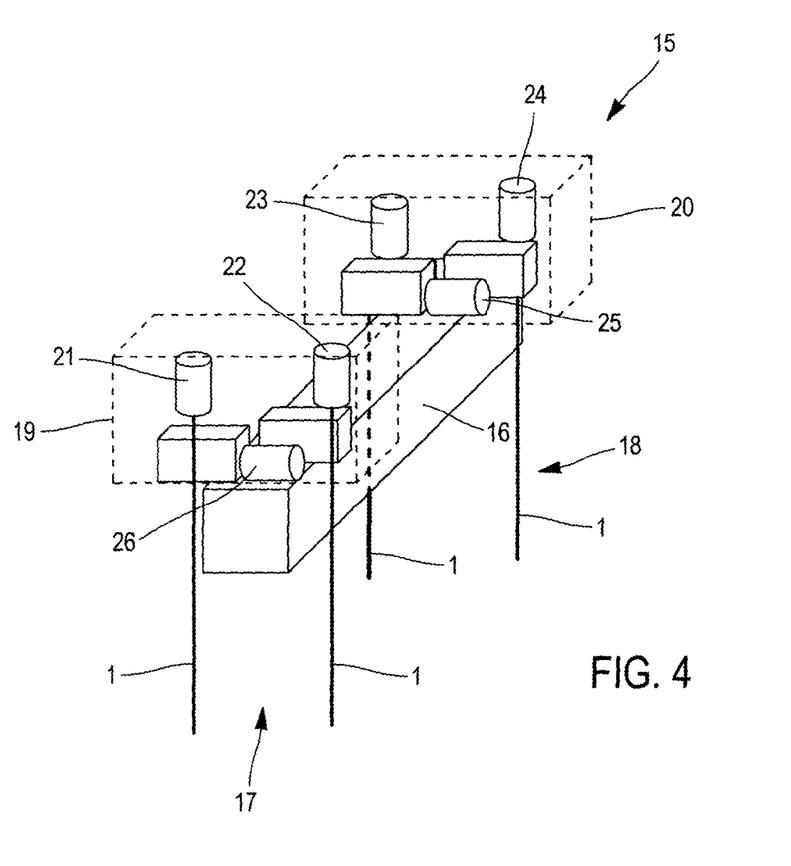
FIG. 4 is a schematic depiction in perspective of the device of the invention.

According to the invention, these resistance measurements can be performed by a device illustrated in FIG. 4 and which can be mounted on any track apparatus.

With reference to that figure, the device 15 comprises a frame 16 on each side of which four penetrometers 1a of the static type extend vertically. The width lo of the frame 16 and the relative positioning of the penetrometers 1 are adjusted so that when the frame 16 is arranged vertically facing a railroad tie which is not visible in this figure, the points of impact of the penetrometers 1a meet the conditions defined hereinabove notably regarding the distance between each point of impact of the penetrometers 1a and the railroad tie in question.

The device depicted in FIG. 4 comprising four penetrometers 1a, the relative arrangement thereof will be that that allows four measurements 11 as defined in the first alternative form depicted in FIG. 2 to be carried out.

Each pair 17, 18 of penetrometers 1 intended to perform compactness measurements on one and the same rail are surmounted by a driving unit 19, 20. Each driving unit 19, 20 comprises two hydraulic, pneumatic driving rams 21, 22; 23, 24 intended to apply the driving energy to each penetrometer 1a.

Moreover, each driving unit 19, 20 comprises a lateral positioning hydraulic ram 25, 26 which allow the penetrometer 1a to which they are connected to be positioned laterally. The actuation of each lateral positioning ram 26 is performed by means of a slot, not visible, made on the lateral face of the driving unit 19, 20 in question. Thus, the distance between the points of impact of the penetrometers 1a and the railroad tie in question is controlled.

The method of the invention thus notably consists in performing at least two measurements of the compactness of the ballast near a railroad tie using penetrometers that measure penetration resistance.

Once these penetration resistance measurements Qd have been performed, a computer determines the mean of these measurements in order to determine the mean penetration resistance $Qd_{mean}$ under a railroad tie, and it is this that defines the condition of the ballast under the railroad tie in question.

The method for predicting the settlement of a layer of railroad ballast of the invention comprises a second step which consists in determining how the condition of the ballast under each railroad tie evolves over time.

To do that, the Applicant has adapted the density relaxation law known to apply to monodispersed glass beads, to the compactness of the ballast according to the number of axle passes over the railroad ties being studied.

The modified relaxation law therefore takes the following form:

$$\tau_N = \tau_\infty \left(1 - \frac{1}{1 + B\ln\left(1 + \frac{N}{No}\right)}\right)$$

where $\tau_N$ indicates the change in compactness of the layer of ballast, expressed in millimeters, as a function of N which is the number of railroad vehicle axle passes over the railroad tie in question, where No corresponds to the following formula:

$$No = a \times \ln\left(\frac{Qd_{0mean}}{p}\right) + b$$

where a is comprised between 46 and 57, and b is comprised between 40 and 50, where $Qd_{0mean}$ is the mean penetration resistance for the railroad tie in question, determined as previously described, and taken at the end of railroad track maintenance or track laying operations, and where p is the pressure under the railroad tie in question, expressed in megapascals, where $\tau_\infty$ corresponds to the following formula:

$$\tau_\infty = Ho(c \times \Gamma + e)$$

where c is comprised between 21 and 32, and e is comprised between 0.0040 and 0.006, where Ho is the thickness of the layer of ballast considered, expressed in millimeters, and where Γ is the reduced intensity of the vibrations to which the ballast is subjected near the railroad tie in question and corresponds to the following formula:

$$\Gamma = \frac{Aw^2}{\frac{pd^2}{m} + g}$$

where A is the amplitude of the elastic vertical sinking of the track,
calculated from a mechanical model or measured, expressed in meters,
where $w^2 = 2\pi f$, f being the frequency of passage of the bogies in hertz,
where p is the load applied by the railroad tie in question to the ballast, expressed in pascals,
where d is the mean diameter of a grain of ballast, expressed in meters, and
where m is the mass of a grain of the ballast, expressed in kilograms, and
where B corresponds to the following formula:

$$B = h \times \Gamma^i$$

where h is comprised between 0.0003 and 0.0014, and i is comprised between −0.3 and −1.15, and
where Γ is the reduced intensity of the vibrations to which the ballast is subjected near the railroad tie in question.

Therefore the way in which the settlement of the layer of ballast of a railroad track evolves can be learned so that track interventions can be carried out when the settlement of the ballast, as determined by the aforementioned settlement law of the invention, becomes too excessive.

The invention claimed is:

1. A method for evaluating the compactness of a layer of railroad ballast near a railroad tie, comprising:
    taking at least two measurements of penetration resistance (Qd) of a ballast near a same railroad tie, and
    calculating a mean value ($Qd_{mean}$) of the at least two measurements of penetration resistance (Qd),
    wherein each of the measurements of penetration resistance (Qd) of the ballast near the railroad tie is carried out using a penetrometer,
    wherein, for each of the respective measurements of penetration resistance (Qd), the driving of the penetrometer into the ballast is carried out by successive drives during which the instantaneous penetration resistance ($Qd_i$) of the penetrometer corresponding to each drive is measured,
    and wherein the penetration resistance (Qd) is obtained as an average of the instantaneous penetration resistance values ($Qd_i$) measured during the successive drives of the penetrometer.

2. The method as claimed in claim 1, wherein each measurement of penetration resistance (Qd) is taken at a maximum distance of five centimeters away from the railroad tie and on each side of the railroad tie.

3. The method as claimed in claim 1, wherein the measurements of penetration resistance (Qd) are separated from one another by at least fifteen centimeters.

4. The method as claimed in claim 1, wherein each of the measurements of penetration resistance (Qd) is taken at a maximum distance of five centimeters away from the rail.

5. The method as claimed in claim 1, comprising taking four measurements of penetration resistance (Qd) of the ballast near the same railroad tie, each of the four measurements being performed on an outside of a rail, on each side of the railroad tie and near the intersection between the railroad tie and the rail.

6. The method as claimed in claim 1, comprising taking eight measurements of penetration resistance (Qd) of the ballast near the same railroad tie, wherein the eight measurements include four first measurements and four second measurements, the four first of the measurements being performed on each side of the railroad tie on an outside of a rail near an intersection between the railroad tie and the rail, and the four second of the measurements being performed on an inside of the rail near the intersection between the railroad tie and the rail.

7. The method as claimed in claim 1,
    wherein the penetrometer is a static penetrometer for which the driving of the penetrometer is carried out by a vertical driving ram, and wherein the compactness of the ballast is determined using a computer, using the following formula:

$$Qd_i = \frac{F}{A}$$

where $Qd_i$ is an instantaneous penetration resistance of the penetrometer per drive,
A is a cross section of a penetration tip expressed in square meters, and
F is a thrust force applied to the penetrometer, expressed in newtons.

8. The method as claimed in claim 1,
    wherein the penetrometer is a dynamic penetrometer comprising a striking head onto which a mass falls at least once to drive into the ballast a conical penetration tip situated at an opposite end from the striking head and connected to the striking head by a rod,
    and wherein the instantaneous penetration resistance of the ballast is calculated using a computer, using the following formula:

$$Qd_i = \frac{E}{A \times e}$$

where $Qd_i$ is an instantaneous penetration resistance for one strike,
E is an energy received on the striking head, expressed in J,
A is a cross section of the tip expressed in square meters,
e is a depth to which the conical tip is driven, expressed in meters.

9. A method for predicting the settlement of a layer of railroad ballast, comprising:
    evaluating a compactness of a layer of railroad ballast by determining a mean value of a penetration resistance ($Qd_{0mean}$) of the ballast near a railroad tie according to the method of claim 1, and
    predicting a settlement of said layer of ballast by applying the following formula:

$$\tau_N = \tau_\infty \left(1 - \frac{1}{1 + B\ln\left(1 + \frac{N}{No}\right)}\right)$$

where $\tau_N$ indicates a change in settlement of the layer of ballast as a function of N which is a number of axle passes over the railroad tie, where No corresponds to the following formula:

$$No = a \times \ln\left(\frac{Qd_{0mean}}{p}\right) + b$$

where a is a value selected in the range of from 46 to 57, and b is comprised between 40 and 50, where $Qd_{0mean}$ is the penetration resistance determined in the evaluating of the compactness of the layer of ballast, and taken at an end of maintenance operations or at a time of laying a railroad track including the railroad tie, and where P is a pressure under the railroad tie, expressed in megapascals, where $\tau_\infty$ corresponds to the following formula:

$$\tau_\infty = Ho(c \times \Gamma + e)$$

where c is a value selected in the range of from 21 to 32, and e is a value selected in the range of from 0.0040 and 0.006, where Ho is a thickness of the layer of ballast, expressed in millimeters, and where $\Gamma$ is a reduced intensity of vibrations to which the ballast is subjected near the railroad tie, and corresponds to the following formula:

$$\Gamma = \frac{Aw^2}{\frac{pd^2}{m} + g}$$

where A is an amplitude of elastic vertical sinking of the track, calculated from a mechanical model or measured, expressed in meters, where $w^2 = 2\pi f$, f being a frequency of passage of bogies in hertz, where P is a load applied by the railroad tie to the ballast, expressed in pascals, where d is a mean diameter of a grain of the ballast, expressed in meters, and where m is a mass of a grain of the ballast, expressed in kilograms, and where B corresponds to the following formula:

$$B = h \times \Gamma^i$$

where h is a value selected in the range of from 0.0003 to 0.0014, and i is a value selected in the range of from −0.3 to −1.15, where $\Gamma$ is the reduced intensity of the vibrations to which the ballast is subjected near the railroad tie.

10. A device for implementing the method for evaluating the compactness of a layer of railroad ballast near a railroad tie, comprising:

at least two static penetrometers able to be driven into the ballast near a same railroad tie, the driving of each penetrometer being carried out by a vertical driving ram, wherein a computer determines a compactness of the ballast using the following formula:

$$Qd_i = \frac{F}{A}$$

where $Qd_i$ is an instantaneous penetration resistance of the penetrometer per drive, A is a cross section of the penetration tip in square meters, and F is a thrust force applied to the penetrometer, expressed in newtons, and wherein the computer averages all the instantaneous penetration resistance values ($Qd_i$) obtained in order to determine the penetration resistance (Qd), wherein the device is configured to implement a method for evaluating the compactness of a layer of railroad ballast near a railroad tie, comprising:

taking at least two measurements of penetration resistance (Qd) of a ballast near a same railroad tie, and calculating a mean value ($Qd_{mean}$) of the at least two measurements of penetration resistance (Qd), wherein each of the measurements of penetration resistance (Qd) of the ballast near the railroad tie is carried out using a penetrometer, wherein, for each of the respective measurements of penetration resistance (Qd), the driving of the penetrometer into the ballast is carried out by successive drives during which the instantaneous penetration resistance ($Qd^i$) of the penetrometer corresponding to each drive is measured, and wherein the penetration resistance (Qd) is obtained as an average of the instantaneous penetration resistance values ($Qd^i$) measured during the successive drives of the penetrometer.

11. The device as claimed in claim 10, comprising a frame intended to be positioned vertically facing and some distance away from a railroad track, and comprising at least four penetrometers fixed to said frame, wherein relative positions of the four penetrometers allow four measurements of the penetration resistance (Qd) of the ballast near the same railroad tie to be carried out.

12. The device as claimed in claim 10, wherein the rate at which each penetrometer is driven down by each vertical driving ram is less than 3 centimeters per second.

13. The device as claimed in claim 10, wherein at least two penetrometers intended to measure the penetration resistance on a same side of a railroad tie are arranged with a lateral positioning ram which allows a lateral positioning of the two penetrometers.

14. The device as claimed in claim 11, wherein the rate at which each penetrometer is driven down by each vertical driving ram is less than 3 centimeters per second.

15. The device as claimed in claim 11, wherein at least two penetrometers intended to measure the penetration resistance on a same side of a railroad tie are arranged with a lateral positioning ram which allows a lateral positioning of the two penetrometers.

16. The device as claimed in claim 12, wherein at least two penetrometers intended to measure the penetration resistance on a same side of a railroad tie are arranged with a lateral positioning ram which allows a lateral positioning of the two penetrometers.

17. The method as claimed in claim 2, wherein the measurements of penetration resistance (Qd) are separated from one another by at least fifteen centimeters.

18. The method as claimed in claim 2, wherein each of the measurements of penetration resistance (Qd) is taken at a maximum distance of five centimeters away from the rail.

19. The method as claimed in claim 3, wherein each of the measurements of penetration resistance (Qd) is taken at a maximum distance of five centimeters away from the rail.

20. The method as claimed in claim 17, wherein each of the measurements of penetration resistance (Qd) is taken at a maximum distance of five centimeters away from the rail.

21. A method for evaluating the compactness of a layer of railroad ballast near a railroad tie, comprising:
  taking at least two measurements of penetration resistance (Qd) of a ballast near a same railroad tie, and
  calculating a mean value ($Qd_{mean}$) of the at least two measurements of penetration resistance (Qd),
  wherein each of the measurements of penetration resistance (Qd) is taken at a maximum distance of five centimeters away from the rail.

22. A device for implementing the method for evaluating the compactness of a layer of railroad ballast near a railroad tie, comprising:
  at least two static penetrometers able to be driven into the ballast near a same railroad tie, the driving of each penetrometer being carried out by a vertical driving ram,
  wherein a computer determines a compactness of the ballast using the following formula:

$$Qd_i = \frac{F}{A}$$

where $Qd_i$ is an instantaneous penetration resistance of the penetrometer per drive,
  A is a cross section of the penetration tip in square meters, and
  F is a thrust force applied to the penetrometer, expressed in newtons,
    wherein at least two penetrometers intended to measure the penetration resistance on a same side of a railroad tie are arranged with a lateral positioning ram which allows a lateral positioning of the two penetrometers.

23. A device for implementing the method for evaluating the compactness of a layer of railroad ballast near a railroad tie, comprising:
  a frame intended to be positioned vertically facing and some distance away from a railroad track, and
  at least four penetrometers fixed to said frame, the penetrometers being able to be driven into the ballast near a same railroad tie, the driving of each penetrometer being carried out by a vertical driving ram, wherein relative positions of the four penetrometers allow four measurements of the penetration resistance (Qd) of the ballast near the same railroad tie to be carried out,
  wherein a computer determines a compactness of the ballast using the following formula:

$$Qd_i = \frac{F}{A}$$

where $Qd_i$ is an instantaneous penetration resistance of the penetrometer per drive,
  A is a cross section of the penetration tip in square meters, and
  F is a thrust force applied to the penetrometer, expressed in newtons, and
    wherein the rate at which each penetrometer is driven down by each vertical driving ram is less than 3 centimeters per second.

* * * * *